United States Patent
Marchal et al.

(10) Patent No.: US 6,853,862 B1
(45) Date of Patent: Feb. 8, 2005

(54) GASTROELECTRIC STIMULATION FOR INFLUENCING PANCREATIC SECRETIONS

(75) Inventors: Benoit Marchal, Maastricht (NL); Warren Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/537,070

(22) Filed: Mar. 28, 2000

Related U.S. Application Data

(60) Provisional application No. 60/168,966, filed on Dec. 3, 1999.

(51) Int. Cl.[7] .................................................. A61N 1/08
(52) U.S. Cl. .......................................................... 607/40
(58) Field of Search ..................................... 607/40, 41

(56) References Cited

U.S. PATENT DOCUMENTS

| | | | |
|---|---|---|---|
| 3,719,183 A | 3/1973 | Schwartz | 128/2 R |
| 4,279,886 A | 7/1981 | Allen | 424/1 |
| 5,188,104 A | 2/1993 | Wernicke et al. | 128/419 R |
| 5,231,988 A | 8/1993 | Wernicke et al. | 128/421 |
| 5,263,480 A | 11/1993 | Wernicke et al. | 607/118 |
| 5,425,751 A | 6/1995 | Baeten et al. | 607/28 |
| 5,716,392 A | 2/1998 | Bourgeois et al. | 607/132 |
| 5,836,994 A | 11/1998 | Bourgeois | 607/40 |
| 5,861,014 A | 1/1999 | Familoni | 607/40 |
| 5,919,216 A | 7/1999 | Houben et al. | 607/72 |

FOREIGN PATENT DOCUMENTS

| | | |
|---|---|---|
| WO | WO 88/ 03389 | 5/1988 |

OTHER PUBLICATIONS

"Stimulatory Effects of the Central Amygdaloid Nucleus on Pancreatic Exocrine Secretion in Rats" Neurosci. Lett. Mar. 14, 1994; 169(1–2):43–6 Hahn et al (abstract).*

Richins, "the Innervation of the Pancreas," J. Comp. Neurol 82:223–236 (1945).

Netter, Frank, "The Ciba Collection of Medical Illustrations," vol. 3 Digestive System, Part III Liver, Billary Tract and Pancreas (1964).

Kang, Sharon Y., et al., "Pancreatic Exocrine–Endocrine Interrelationship, Clinical Implications", Pancreas Update 0889–8553 (Sep., 1999), vol. 28, No. 3.

Holst, Jens et al., "Nervous Control of Pancreatic Secretion in Pigs", Acta Physiol. Scand. 105, 33–51 (1979).

Fiorucci et al., "Duodenal Osmolality Drives Gallbladder Emptying in Humans, Digestive Diseases and Sciences", vol. 35. No. 6, pp. 698–704 (Jun. 1990).

Koch, Kenneth et al., Electrogastrography, An Illustrated Guide to Gastrointestinal Motility $2^{nd}$ Ed., pp. 290–307 (1993).

Durand, "Electric Stimulation of Excitable Tissue," The Biomedical Engineering Handbook, Chapter 17, pp. 229–251 (1995).

Davison, et al., "Plasma Osmolality and Urinary Concentration and Dilution During and After Pregnancy: Evidence that lateral recumbency inhibits maximal urinary concentration ability," British Journal of Obstetrics & Gynecology, 88(5):472–479 (May, 1981).

Boissonade et al., "Fos expression in ferret dorsal vagal complex after periphreal emetic stimuli," The American Physiological Society, 0363–6119/94 (1994).

* cited by examiner

*Primary Examiner*—Mark Bockelman
(74) *Attorney, Agent, or Firm*—Eric R. Waldkoetler; Keith M. Campbell; Thomas F. Woods

(57) ABSTRACT

A gastroelectric stimulator comprises a neurostimulator for producing a stimulation signal, at least one electrical lead, and at least two electrical contacts. The electrical lead has a proximal end and a distal end, the proximal end being connected to the neurostimulator and the distal end positionable in a lead position within the patient's abdomen. The electrodes are carried near the electrical lead distal end. The electrodes are electrically connected through the electrical lead to the neurostimulator to receive the stimulation signal and convey this signal to an electrode position within the patient's digestive system. The stimulation signal is adapted to influence pancreatic secretions.

6 Claims, 11 Drawing Sheets

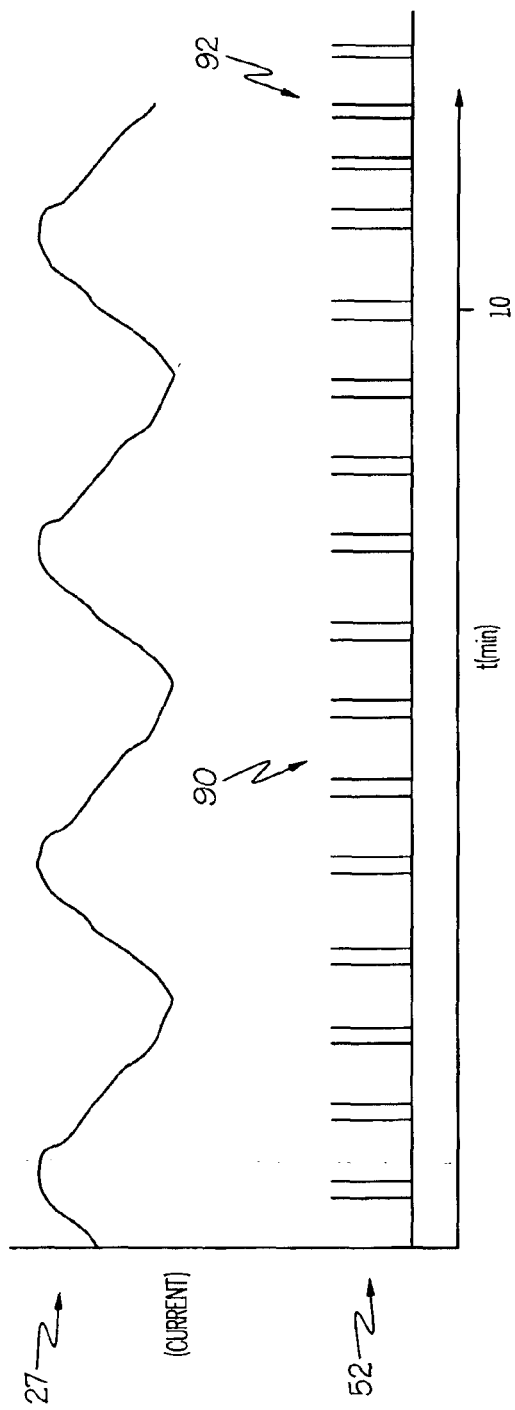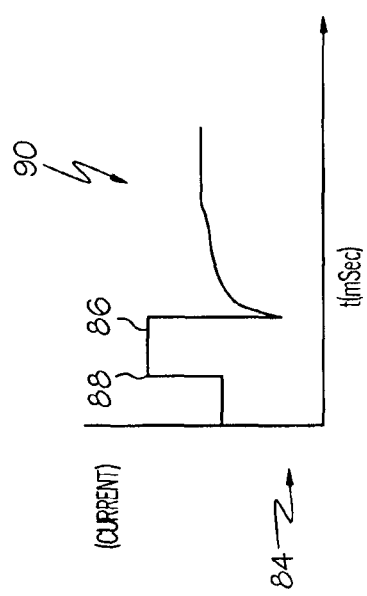

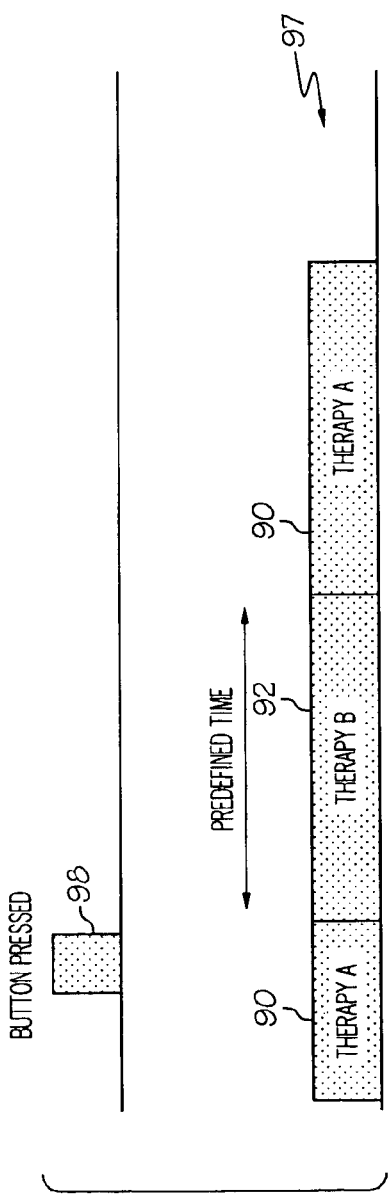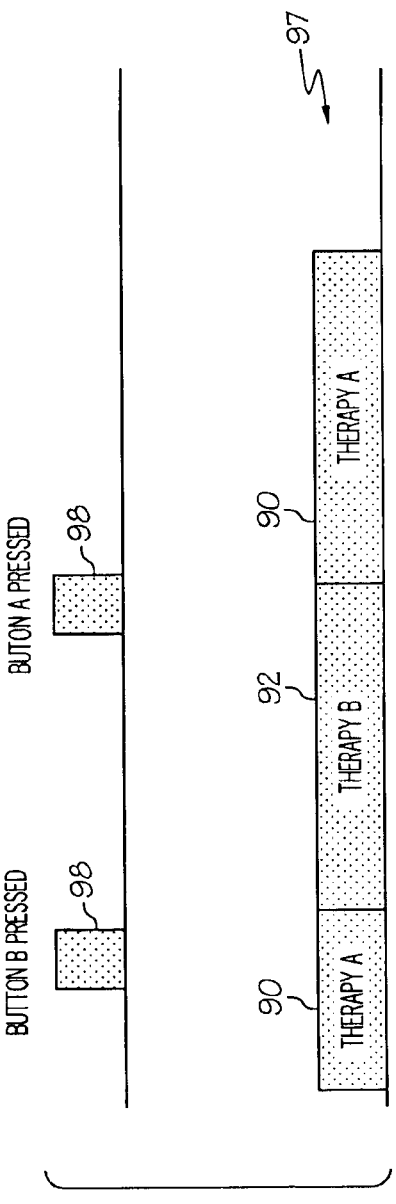

GASTROELECTRIC STIMULATION FOR INFLUENCING PANCREATIC SECRETIONS

RELATED APPLICTIONS

This application claims priority to provisional application Ser. No.: 60/168,966, filed Dec. 3, 1999.

BACKGROUND OF THE INVENTION

This disclosure relates to medical devices used to electrically stimulate the digestive system and more particularly electrical stimulation to influence pancreatic secretions.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. One medical condition that has been difficult to treat is the wide variety of pancreatic diseases.

The pancreas is an organ that has both exocrine and endocrine functions. Pancreatic exocrine functions include secreting enzymes and bicarbonate into the duodenum where they aid in digestion and absorption of nutrients. Pancreatic exocrine conditions include pancreatitis, inflammation of the pancreas, and cystic fibrosis, and pancreatic exocrine conditions can affect other gastrointestinal tract conditions such as nausea, vomiting, malabsorption syndrome, and pain. In addition to exocrine functions, the pancreas also performs endocrine functions. Pancreatic endocrine tissue is made up of pancreatic islets that produce hormones that control the metabolic functions of other organs. Pancreatic endocrine conditions include diabetes mellitus and pancreatitis.

Previous treatments for pancreatic exocrine and endocrine conditions using drugs and surgery do not satisfactorily treat some patient conditions. Drugs used to treat pancreatic conditions include insulin and pancreatic enzymes, and surgery used to treat pancreatic conditions includes pancreatic resection and transplant.

One previous treatment for pancreatic endocrine conditions involved applying an electrical stimulation signal to the vagus nerve to increase pancreatic endocrine secretions such as described in U.S. Pat. No. 5,231,988, "Treatment Of Endocrine Disorders By Nerve Stimulation" by Wernicke et al (Aug. 3, 1993). Vagal stimulation therapy is difficult to achieve and can adversely stimulate other organs. The electrodes used with vagal stimulation can also damage the vagal nerve by creating lesions.

Another previous treatment for pancreatic endocrine conditions involved applying an electrical stimulation signal directly to the pancreas such as described in U.S. Pat. No. 5,919,216, "System And Method For Enhancement Of Glucose Production By Stimulation Of Pancreatic Beta Cells" by Houben et al. (Jun. 6, 1999). Direct pancreatic stimulation therapy is not always effective in stimulating the entire pancreas.

For the foregoing reasons, there is a need for a neurostimulator configured to apply a stimulation signal to a patient's digestive system to influence pancreatic exocrine and endocrine secretions.

SUMMARY OF THE INVENTION

A stimulation signal is applied to a patient's digestive system to influence the patient's pancreatic output. The stimulation signal is applied by a neurostimulator that has at least one electrical lead positionable in a patient's abdomen. The lead carries at least two electrodes positionable for contact with the patient's digestive system. In one version of the invention, the stimulation signal is adapted to influence pancreatic exocrine secretions. In another version of the invention, the stimulation signal applied to the patient's stomach and adapted to influence pancreatic endocrine secretions.

BRIEF DESCRIPTION OF THE DRAWINGS

FIGS. 6a–b show general stimulation signal diagrams;

FIGS. 8a–b show therapy diagrams;

DETAILED DESCRIPTION

Figure 1:
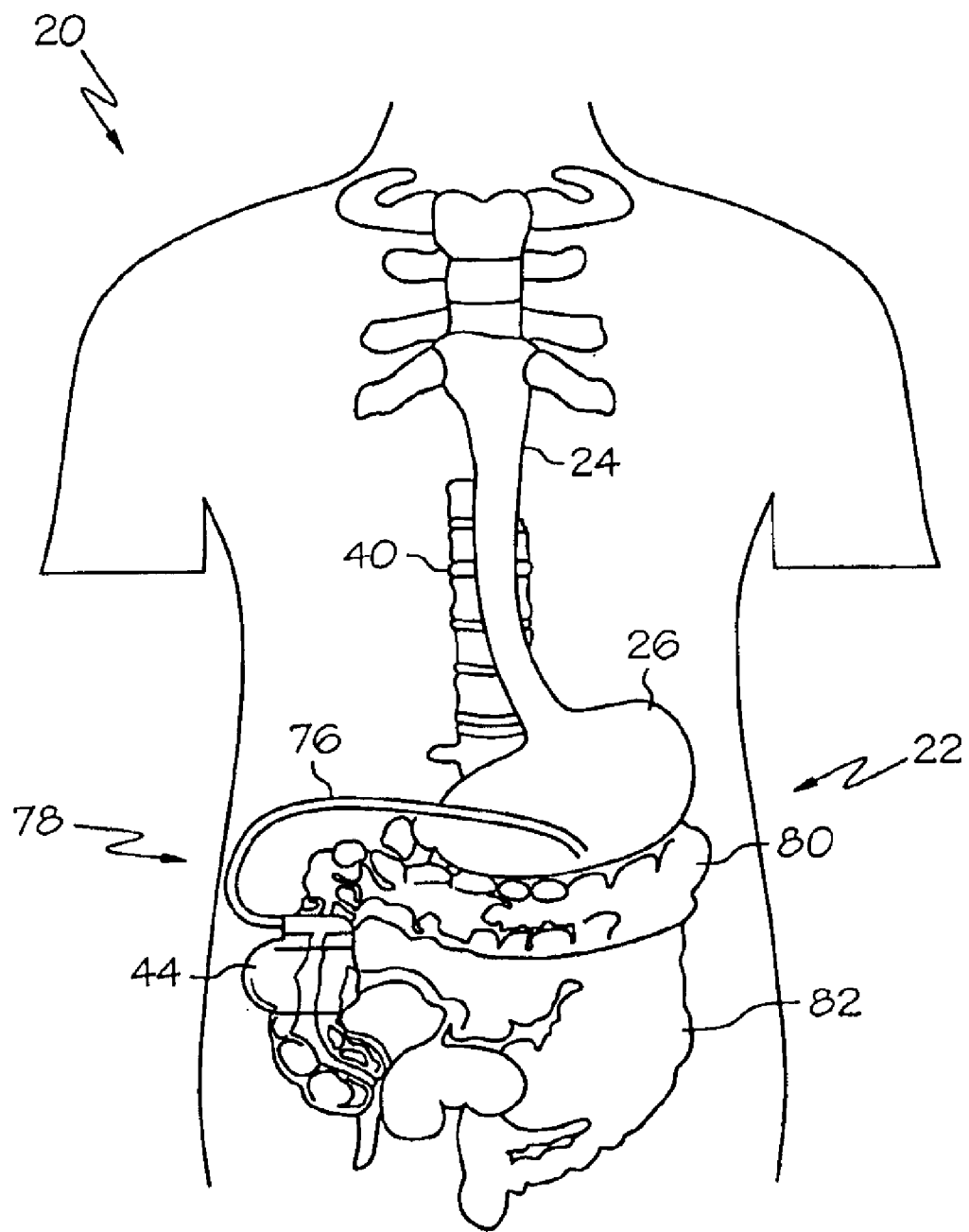
FIG. 1 shows an environment of the gastroelectric stimulator for influencing pancreatic secretions.
Figure 2:
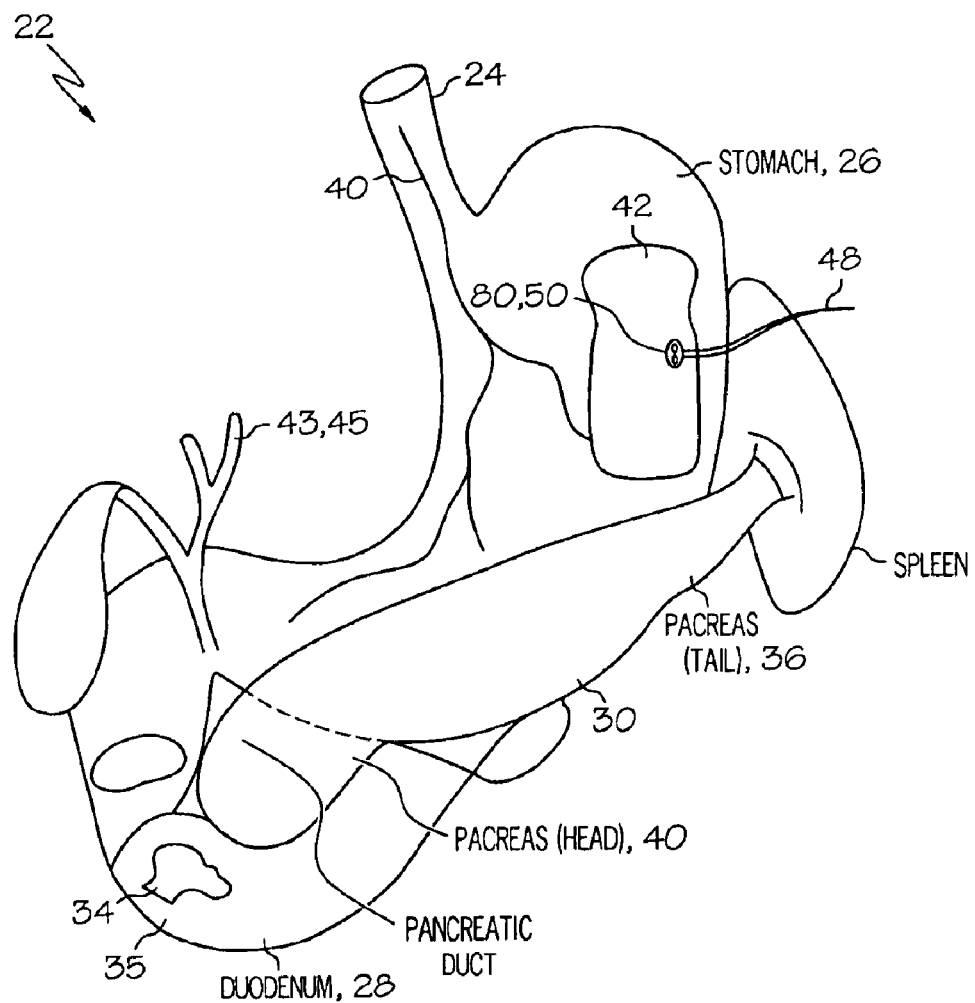
FIG. 2 shows a more detailed environment of the gastroelectric stimulator.

FIGS. 1 and 2 show the general environment for using gastroelectric stimulation to influence pancreatic secretions. A patient's 20 digestive system 22 includes the esophagus 24, stomach 26, duodenum 28, and pancreas 30. The stomach 26 plays a central role in influencing the digestive system 22 by acting as a pacemaker through myoelectrical activity that creates a variety of signals such as a gastric slow wave 27 (FIG. 6a) of about 3.0 cycles per minute as described in the following publication: Kenneth Koch et al., Electrogastrography, An Illustrated Guide To Gastrointestinal Motility $2^{nd}$ Ed., pp. 290–307 (1993).

The duodenum 28 is the first division of the small intestine that is about 25.0 cm in length and includes the pars descendens into which the pancreatic 30 ducts open. Duodenal chyme 34 is a semi-fluid mass of partly digested food with a typical normal daily volume of about 4.0 to 7.0 liters that passes from the stomach 26 into the duodenum 28. The duodenum 28 has osmoreceptors 35 that respond to osmotic pressure in the duodenum 28 by sending nerve impulses that can cause nausea and vomiting when the osmoreceptors 35 sense a significant osmotic imbalance in the duodenum 28.

The pancreas 30 has a tail 36, a body 38, a head 40, a duct of Santorini and a duct of Wirsung. The duct of Wirsung is the principal duct that drains most of the pancreas 30 that starts in the tail 36 by the confluence of several small ducts and extends into the head 40 where it terminates at the duodenum 28 papilla. The duct of Santorini is an accessory duct that drains a small upper anterior part of the head 40 and terminates in the duodenum 28 at a small accessory papilla. The exocrine pancreas 30 has acini cells and a ductal system of intralobular and intercalated ducts organized into lobules that secrete enzymes and bicarbonate into the duodenum 28 where they aid in digestion and absorption of nutrients.

Pancreatic 30 interdigestive secretion cycles in temporal coordination with gastrointestinal motility. Pancreatic 30 secretions include exocrine and endocrine secretions.

Pancreatic 30 exocrine secretions mainly assist in digestion and include bicarbonate and enzymes such as trypsin, chymotrypsin, amylase, and lipase. Daily pancreatic 30 exocrine secretion is typically in the range from 1.0 to 2.0 liters, and the secretions are dominantly isotonic. Pancreatic 30 endocrine secretion regulate metabolism and include enzymes such as insulin, glucagons, somatostatin, and pancreatic polypeptide. Pancreatic 30 secretions are responsive to nervous control and gut hormones.

The pancreas 30 and other intra-abdominal organs are innervated by the sympathetic and parasympathetic branches of the autonomic nervous system. Sympathetic innervation is supplied by the splanchnic nerves, and parasympathetic innervation is supplied by the vagus nerves 41. Pancreatic 30 acinar and islet cells are innervated only directly through parasympathetic nerves, and pancreatic 30 blood vessels are innervated solely by sympathetic nerves. All nerves of the pancreas 30, both afferent 43 and efferent 45, pass through the celiac plexus. Pancreatic 30 secretion can be affected by both natural simulation and electrical stimulation. Pancreatic 30 exocrine and endocrine secretion are controlled by the central and enteric nervous system that are stimulated during meal ingestion, and pancreatic 30 secretion are also influenced by gut hormones that are released after meal ingestion. Pancreatic 30 innervation is further described in the following article by Richins, "The innervation of the pancreas", J. Comp. Neurol 82:223–236 (1945). Pancreatic 30 secretion can also be influenced by electrical stimulation.

Electrical stimulation applied to nerves innervating the pancreas 30, organs that are commonly innervated with the pancreas 30, or the pancreas 30 itself can influence pancreatic 30 secretions. When electrical stimulation is applied to nerves, existing natural signals can be blocked or altered as described in Durand, Dominique M., "Electric Stimulation of Excitable Tissue", The Biomedical Engineering Handbook, Chapter. 17, pp. 229–251 (1995). One location to apply electrical stimulation to influence pancreatic 30 secretions is the stomach 26 because the stomach 26 shares significant common innervation with the pancreas 30.

Electrical stimulation of the vagus nerve 41 and the digestive system 22 can influence pancreatic 30 secretions. It is believed that electrical stimulation of the vagus nerve 41 or digestive system 22 causes impulses that result in pancreatic 30 stimulation. Impulses caused by electrical stimulation of the vagus nerve 41 or digestive system 22 can travel by means of both afferent 43 and efferent 45 pathways to the pancreas 30. Some impulses can travel from the digestive system 22 along a vagal 41 afferent pathway to the brain and then along an efferent pathway from the brain to the pancreas 30. The stomach 26 is a location in the digestive system 22 well suited for stimulation because the wall of the stomach 26 is suitable for making electrical connections and the stomach 26 is well enervated by the vagus nerve 41. The stomach 26 pacemaker region 42 is particularly well enervated by the vagus nerve 41 and other portions of the digestive system 22. Electrical stimulation can be applied by a neurostimulator 44 a configured as a gastroelectric stimulator 46.

Figure 3:
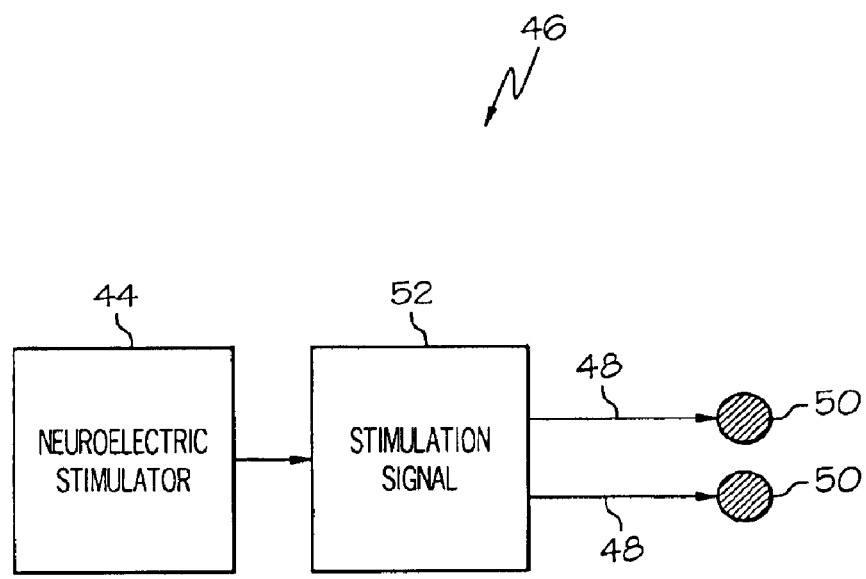
FIG. 3 shows a block diagram of a gastroelectric stimulator.

FIG. 3 shows a block diagram of a gastroelectric stimulator 46. The gastroelectric stimulator 46 comprises a neurostimulator 44, an electrical lead 48, electrodes 50, and a stimulation signal 52 produced by the neurostimulator 44.

Figure 4:
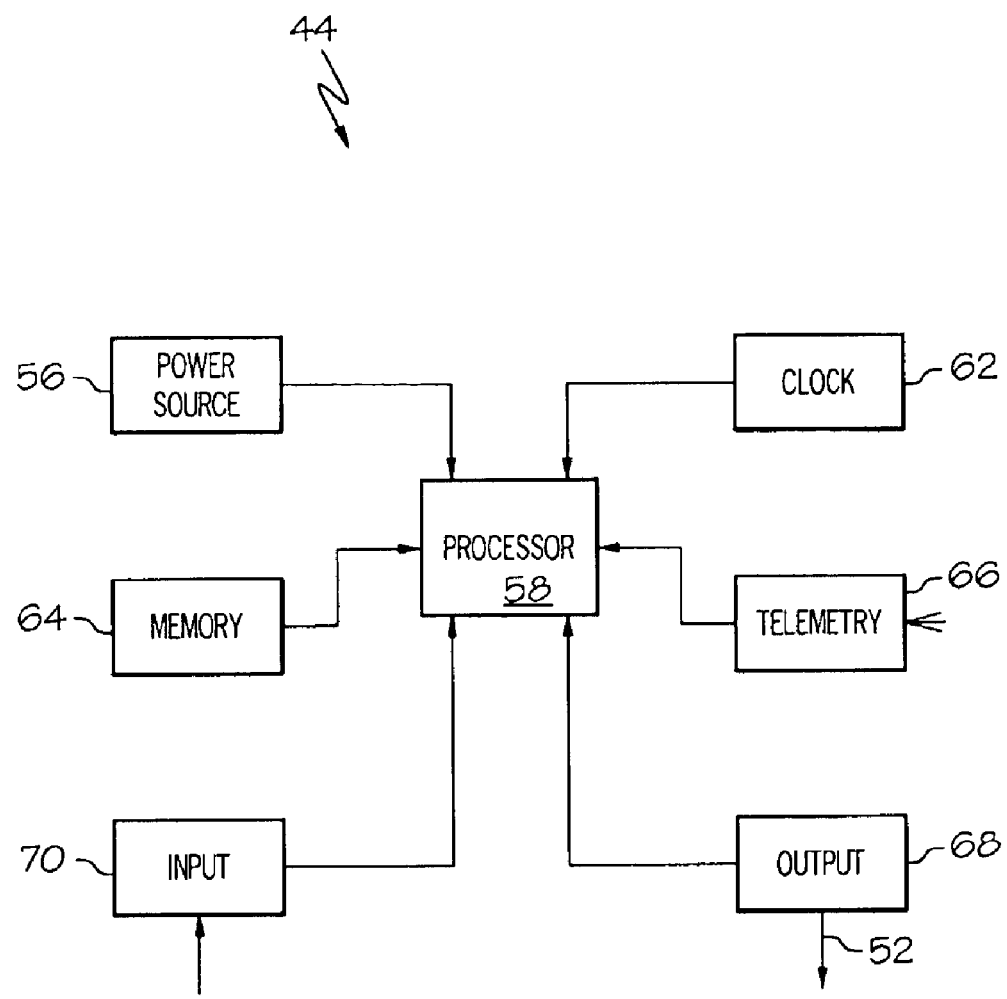
FIG. 4 shows a block diagram of a neurostimulator.

The gastroelectric stimulator 46 can also include a sensor 54 that measures a patient 20 parameter such as temperature, activity, and blood pressure and feeds this information via a sensor signal 55 to the neurostimulator 44, so the stimulation signal 52 can be adjusted if desired. FIG. 4 shows a block diagram of a neurostimulator 44, also known as a pulse generator. The neurostimulator 44 produces a stimlation signal 52 that can be used to perform neuromodulation at to reduce pain, decrease tremors, control incontinence, and perform other medical therapies. The neurostimulator 44 includes a power source 58, a processor 60, a clock 62, memory 64, telemetry 66, an output 68, and an input 70. The neurostimulator processor 60 can be programmed to modify parameters of the stimulation signal 52 such as frequency, amplitude, and pulse width. An input 70 is typically a sensor 54 (FIG. 3) that senses a parameter and feeds that information to the processor 58 which can make changes in the stimulation signal 52 based upon an algorithm stored in the processor 58 or memory 64. The neurostimulator 44 can be surgically implanted such as in a subcutaneous pocket in the abdomen 78 (FIG. 1) or positioned outside the patient 20. An example of a neurostimulator 44 is the Itrel® 3 Model 7425 available from Medtronic, Inc. The neurostimulator 44 is typically programmed with a physician programmer such as a Model 7432 also available from Medtronic, Inc.

Figure 5:
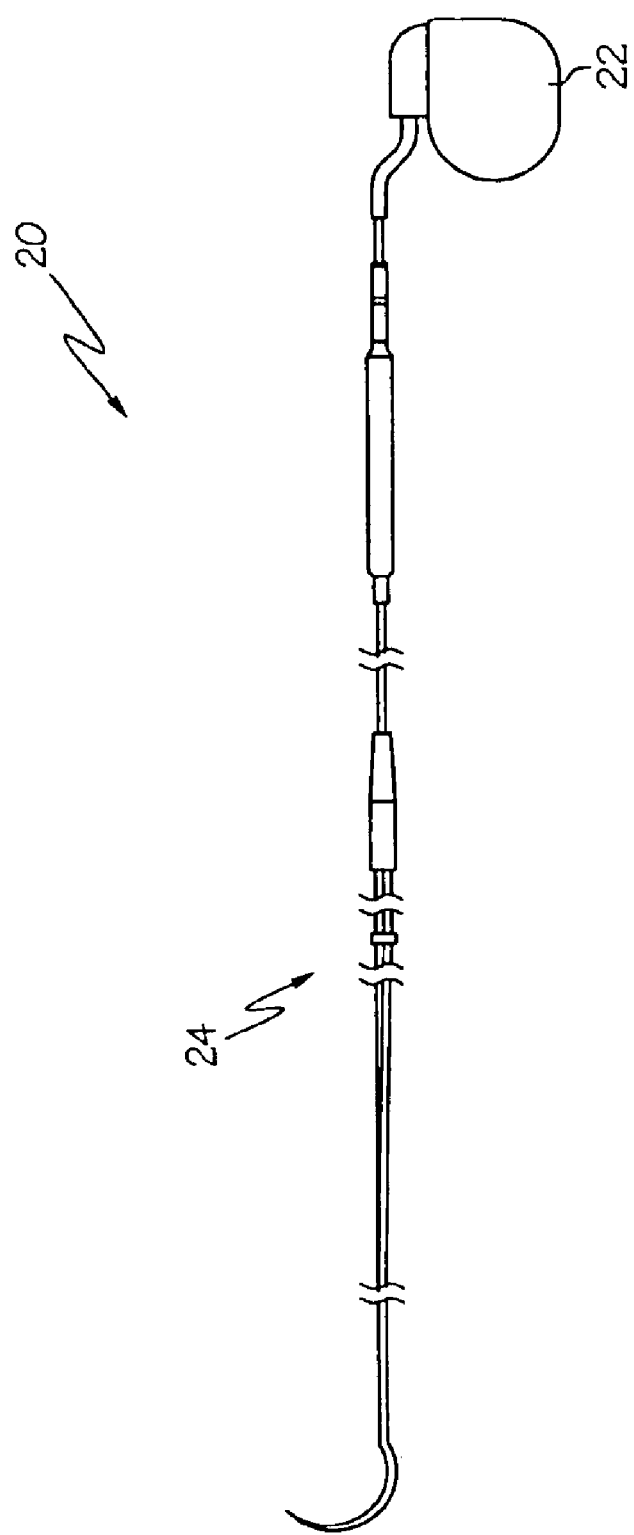
FIG. 5 shows a neurostimulator, an electrical lead, and electrodes.

FIG. 5 shows the neurostimulator 44, an electrical lead 48 and electrodes 50. There is at least one electrical lead 48 but additional electrical leads 48 can be used. The electrical lead 48 has a proximal end 72 and a distal end 74. The proximal end 72 is connected to the neurostimulator 44 and the distal end 74 is positionable in a lead position 76 (FIG. 1) within the patient's abdomen 78 (FIG. 1). The electrical lead 48 has one or more electrical conductors that are surrounded by a biocompatible insulator. The electrical leads 48 are leads suitable for a neurostimulator 44 such as Model 4300 leads available from Medtronic, Inc. The electrical leads 44 are surgically inserted into a patient 20, using a surgical technique such as laparotomy or laparoscopy, with the proximal end 72 located near the neurostimulator 44 and the distal end 74 located near the desired stimulation site. The lead 48 can be placed in the lesser curvature of the stomach 26 corpus via a preexisting percutaneous gastrostomy site or inserted with the proximal end 72 extending outside the patient's 20 body. The electrical lead 48 and electrodes 50 are selected with an impedance to produce a peak pulse current in the range from about 0.01 mA to 100.0 mA.

The electrodes 50, also known as electrical contacts, comprise at least two electrodes 50 and additional electrodes 50 can be used. The electrodes 50 are carried on the electrical lead 48 near the distal end 74. The electrodes 50 are electrically connected through the electrical lead 48 to the neurostimulator 44. The electrodes 50 receive a stimulation signal 52 from the neurostimulator 44 and convey this to an electrode position 80 within the patient's digestive system 22. The electrodes 50 can be configured as monopolar electrodes 50 with one electrode 50 per lead 48 or as multipolar electrodes 50 with more than one electrode 50 per lead 48. The electrodes 50 are attached to the electrical lead 48 prior to implantation and navigated to a point near the desired stimulation site. The electrodes 50 are made from a biocompatible conductive material such as platinum-iridium. The electrodes 50 are implanted into the muscle wall of the stomach 26 such as 0.5 cm to 10.0 cm apart on the greater curvature at the limit of the corpus-antrum.

FIG. 2 shows electrode 50 placement within a patient's abdomen 78 in the environmental view of a gastroelectric stimulator 46. The electrodes 50 are placed in electrical contact with the desired organ such as the vagus nerve 41, stomach 26, pancreas 30, intestine 82, or other digestive system 22 organ. The electrode 50 location is selected based upon the enervation with the vagus nerve 41 and the digestive system 22 along with the suitability for electrode 50 connection. Areas suitable for electrode 50 connections are areas easily assessable by surgery that are substantial enough to secure and retain the electrodes 50. Some of the specific electrode 50 locations that are well enervated, accessible, and substantial are: the stomach 50 and the intestine 82.

FIG. 6a shows a stimulation signal 52 diagram, and FIG. 6b shows a single stimulation pulse 84. Stimulation signal 52 parameters are selected to influence pancreatic 30 secretion through direct stimulation or by stimulating afferent nerves 43 or efferent nerves 45 or both afferent 43 and efferent nerves 45. The stimulation signal 52 has a frequency selected to influence pancreatic 30 secretion such as from about 0.2 pulses per minute to 18,000 pulses per minute. The stimulation signal 52 has a pulse width selected to influence pancreatic 30 secretion such as from about 0.01 mSec to 500.0 mSec. The stimulation signal 52 has a peak amplitude selected to influence pancreatic 30 secretion such as from about 0.01 mA to 100.0 mA. The stimulation signal 52 is charge balanced for biocompatibility. The stimulation signal 52 can consist of at least a first stimulation signal 90 and at least a second stimulation signal 92. The first stimulation signal 90 has parameters selected to influence pancreatic 30 secretion. The second stimulation signal 92 can be different from the first stimulation signal 90 and has also has parameters also selected to influence pancreatic 30 secretion. There can also be additional stimulation signals 52 with parameters different from the first stimulation signal 90 and different from the second stimulation signal 92. Both the first stimulation signal 90 and the second stimulation signal 92 can be null signals. The stimulation signal 90 can be configured for a particular purpose such as a pancreatic increase signal 94 and a pancreatic decrease signal 96.

Figure 7B:
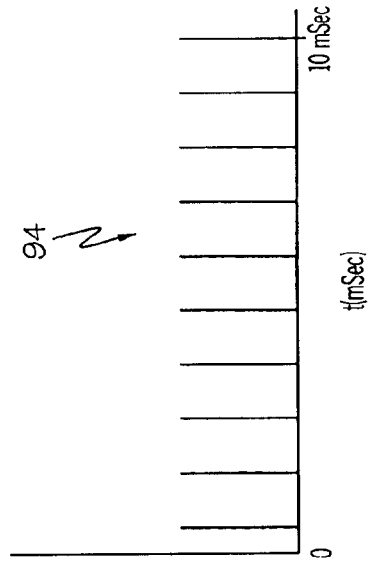
FIGS. 7a–c show more specific stimulation signal diagrams.
Figure 7C:
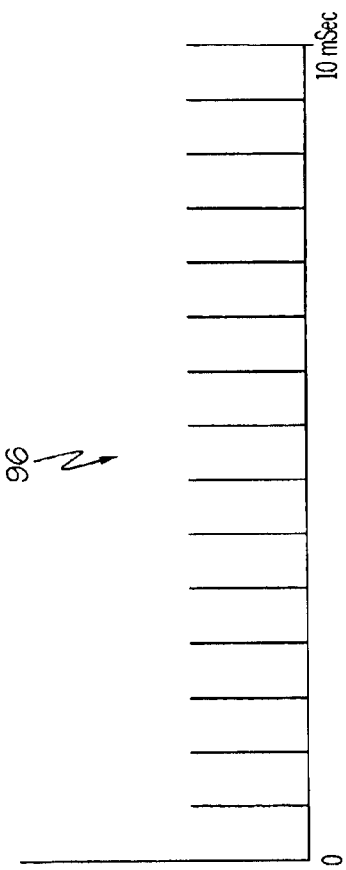
Figure 7A:
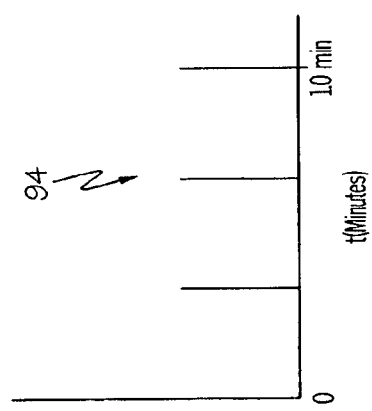

FIGS. 7a–b show an increase signal 94 diagram. The pancreatic increase signal 94 is configured to increase pancreatic 30 secretion and has a frequency and amplitude selected to signal the pancreas 30 to increase the production of exocrine secretions and endocrine secretions. The increase signal 94 frequency is in the range from about 3.0 pulses per minute to 6,000 pulses per minute. Other parameters of the increase signal 94 can be similar to the parameters of the stimulation signal 52. The increase signal 94 can be applied in a therapy such as to improve normal digestion, sleep, exercise, decrease nausea and vomiting, or decrease pain.

FIG. 7b shows a decrease signal 96 diagram. The pancreatic decrease signal 96 is configured to decrease pancreatic 30 secretion. The decrease signal 96 has a frequency and amplitude selected to signal the pancreas 30 to decrease the production of exocrine secretions and endocrine secretions. The decrease signal 96 frequency is in the range greater than 6,000 pulses per minute. Other parameters of the decrease signal 96 can be similar to the parameters of the stimulation signal 52.

FIGS. 8a–b show therapy diagrams. The stimulation signal 52 can be configured and sequenced in wide variety of forms in addition to the increase signal 94 and the decrease signal 96 and sequenced to create a therapy signal 97. The configuration and sequencing of the stimulation signal 52 can be programmed or controlled by the patient 20. For example, a patient 20 may wish to only influence pancreatic secretion upon activating a control button 98 the following conditions: for a period of time after consuming a meal, upon sensation of pain, or upon sensation of nausea.

A therapy 97 to treat gastroparesis and other upper gastrointestinal tract motor disorders applies an pancreatic secretion increase signal 94 for a period of time after ingestion of a meal. A therapy 97 to treat pancreatitis applies a pancreatic secretion increase signal 94 or a decrease signal 94 or both an increase signal 94 and a decrease signal 96 at different times. Therapies 97 can also be controlled by measuring a patient 20 condition related to the desired therapy 97 such as the degree of pancreatic 30 secretion, pH, motion, duodenum 28 osmolality, impedance, and pancreatic 30 electrical activity, pain, weight, nausea, or vomiting. The patient 20 condition can be measured with a sensor 54 that generates a sensor signal 55. The sensor signal 55 could then be inputted to the neurostimulator 44 to use in controlling the stimulation signal 52. The patient 20 condition can also be measured by the patient 20 herself or by a clinician. The patient 20 or clinician would then use the measured patient condition to control the stimulation signal 52. Effective therapies 97 for treating vomiting, also known as emesis, and nausea in certain persons such as pregnant women and athletes have be elusive because a significant underlying cause for the condition has not been sufficiently understood.

Many pregnant women experience nausea and vomiting, known as morning sickness, during the early stage of their pregnancy. In some women, morning sickness is so severe that they are hospitalized during long portions of their pregnancy and sometime require a feeding tube or intravenous feeding to obtain nourishment. Currently, it is believed there is no U.S. Federal Drug Agency (FDA) approved medical device for treating morning sickness. Some athletes after long or intensive exercise also experience nausea and vomiting that is difficult treat, and female athletes appear to be more susceptible. If the underlying cause for nausea and vomiting experienced by pregnant women and athletes were understood, a therapy could be developed to treat their condition and others having the same cause for nausea and vomiting.

For pregnant women experiencing morning sickness, it has been found that their plasma osmolality reaches a minimum approximately ten weeks after the start of their pregnancy as described in the following article: Davidson J M et al., "Plasma osmolality and urinary concentration and dilution during and after pregnancy: evidence that lateral recumbency inhibits maximal urinary concentration ability", British Journal of Obstetrics & Gynaecology, 88(5):472–9 (May 1981). This point of minimum osmolality also corresponds to the most intense period of morning sickness for many women. For athletes experiencing nausea and vomiting, the cause may be hyponatremia resulting from a lake of sodium ions in the stomach muscle. Additionally, patients with nonulcerative dyspepsia have experienced nausea and vomiting during intraduodenal infusion of saline as described in the following article: Fiorucci et al., "Duodenal Osmolality Drives Gallbladder Emptying in Humans", Digestive Diseases and Sciences, Vol 35, No. 6, pp. 698–704 (June 1990). Further, dogs experience nausea and vomiting when they receive an intraduodenal hypertonic saline solution as described in the following article: Fiona Boissonade et al., "Fos expression in ferret dorsal vagal complex after peripheral emetic stimuli", The American Physiological Society, 0363-6119/94 (1994). A significant cause for vomiting and nausea for pregnant women experiencing morning sickness and for some athletes after long or intensive exercise appears to be a digestive system osmotic imbalance brought about by physical stress such as pregnancy or exercise.

A digestive system 22 osmotic imbalance experienced by pregnant women with morning sickness or athlete after strenuous exercise typically occurs when that stomach 26 contains an excessive amount of sodium ions creating an hypertonic solution. An hypertonic solution has a greater osmotic pressure than a reference solution such as intestinal fluid and causes cells to shrink. Sodium ions pass from the stomach 26 into the duodenum 28 as part of the typical 4.0 to 7.0 liters of chyme. The difference in osmolality between the inside of the duodenum 28 and outside the duodenum 28 in the blood stimulate osmotic receptors 35 in the duodenum 28 that cause nausea and can induce vomiting.

The nausea and vomiting induced by osmotic receptors in the duodenum 28 sensing hypertonicity in the duodenum 28 can be reduced by reducing the hypertonicity caused by the osmotic imbalance. Osmotic receptors 35 in the duodenum 28 are exposed to about 4.0 to 7.0 liters daily of chyme 34 received from the stomach 26 and about 1.0 to 2.0 liters daily of pancreatic 30 exocrine secretion through the hepato-pancreatic ampulla. Since pancreatic 30 exocrine secretion sodium concentration is typically constant and isotonic whatever the secretory rate, increasing pancreatic 30 exocrine secretion will decrease the hypertonicity of duodenal chyme 34 sensed by duodenal 28 osmotic receptors 35. A decrease in hypertonicity will decrease the osmotic imbalance sensed by the osmotic receptors and reduce the nausea and vomiting caused by an osmotic imbalance. Pancreatic 30 exocrine secretion can be increased using a gastroelectric stimulator 46 configured to increase pancreatic 30 exocrine secretions as described earlier.

Figure 9:
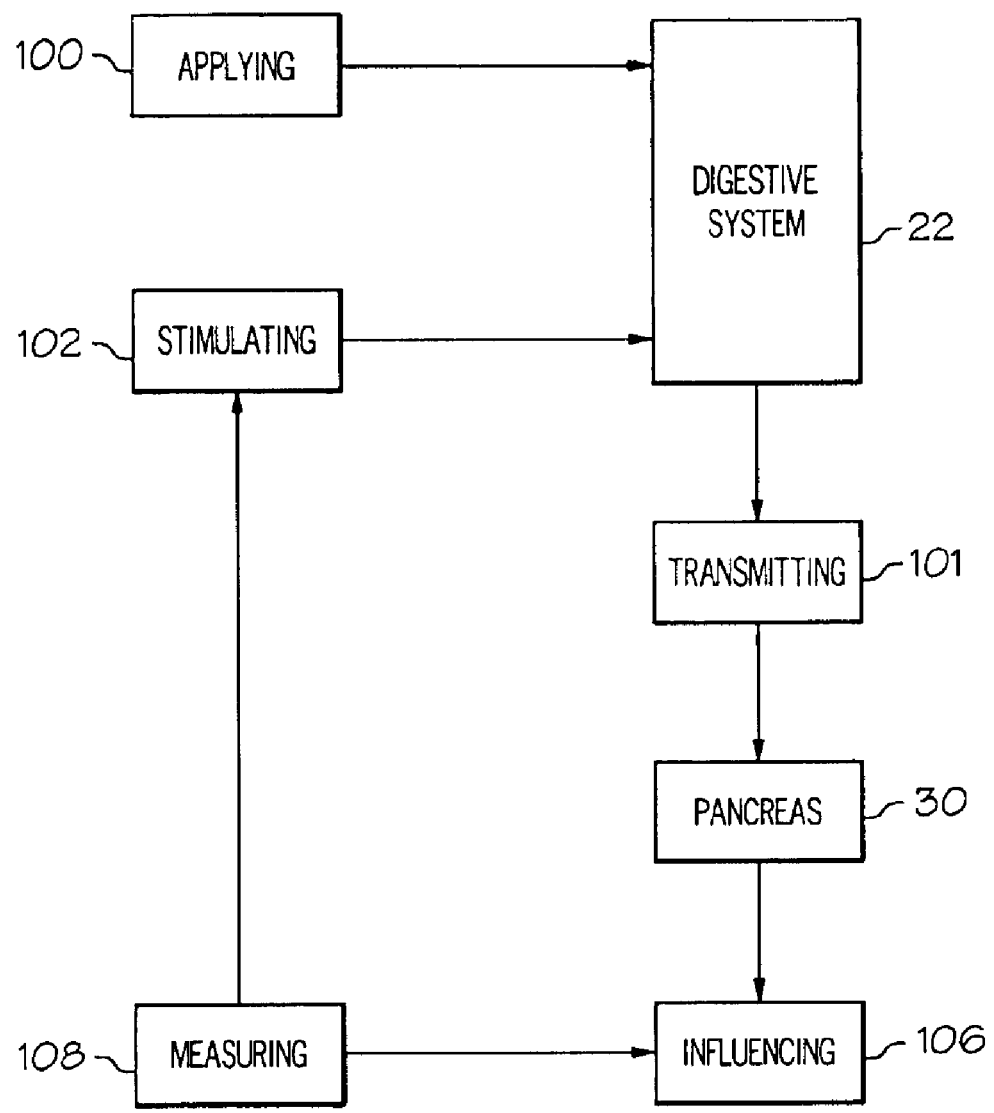
FIG. 9 shows a flow diagram of a method for influencing pancreatic secretions; and, FIGS. 10a–b show graphs depicting test results of the gastroelectric stimulation for influencing pancreatic secretions.

FIG. 9 shows a flow diagram of a method for influencing pancreatic secretions. The method for influencing pancreatic exocrine secretions begins by applying 100 the electrodes 50 to the digestive system 22 of the patient 20 that are coupled by the lead 48 to a neurostimulator 44. Stimulation is applied by stimulating 102 the digestive system 22 with a stimulation signal 52 generated by the neurostimulator 44 and conveyed through the lead 48 to the electrodes 50 contacting the digestive system 22. The digestive system 22 stimulation is transmitted 104 to the pancreas 30 of the patient 20. Finally simulation of the pancreas 30 influences 106 pancreatic 30 exocrine secretion. Measuring 108 the degree of pancreatic influence 106 can be used to adjust stimulation 106 to achieve the desired pancreatic influence 106.

Figure 10A:
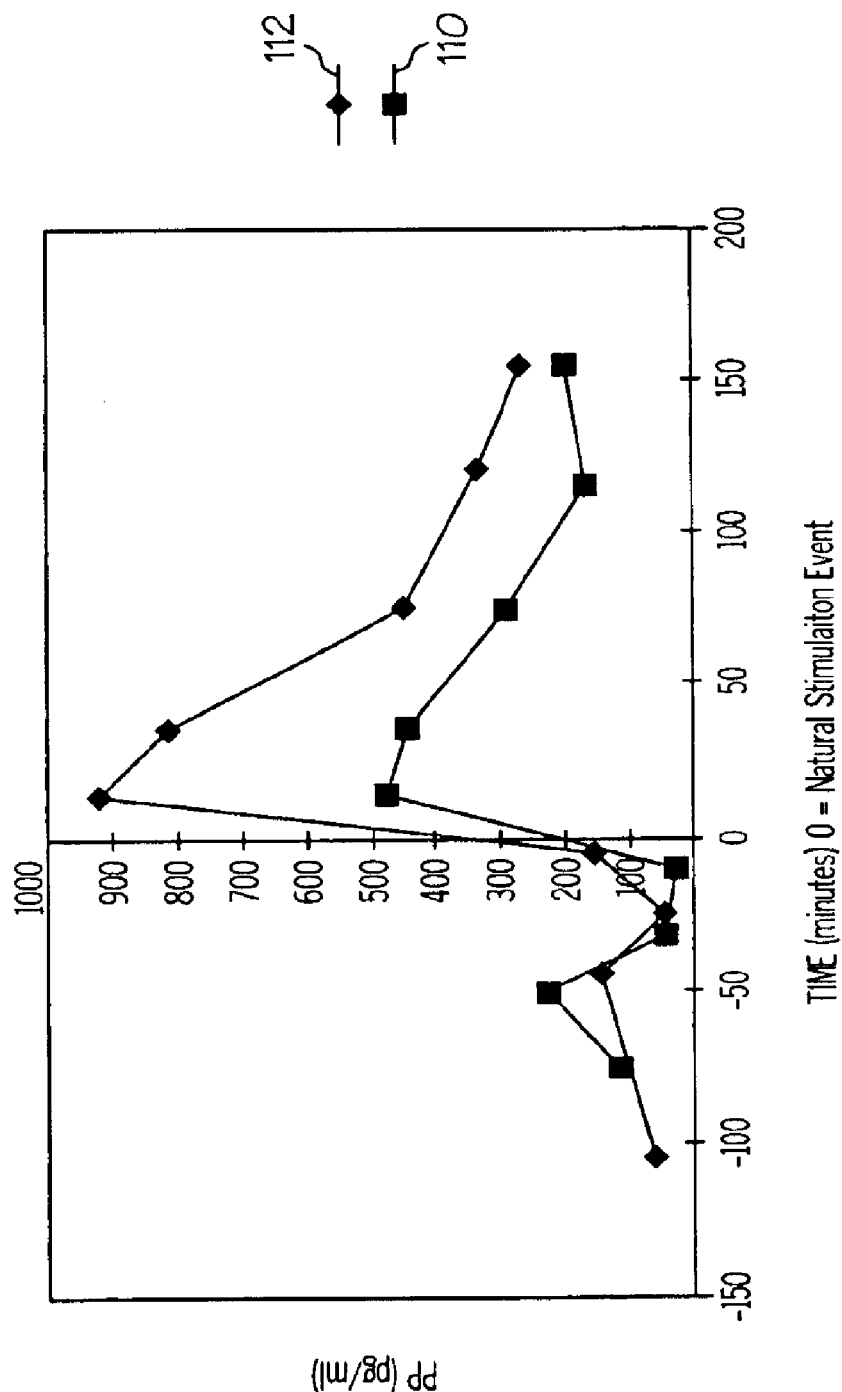
Figure 10B:
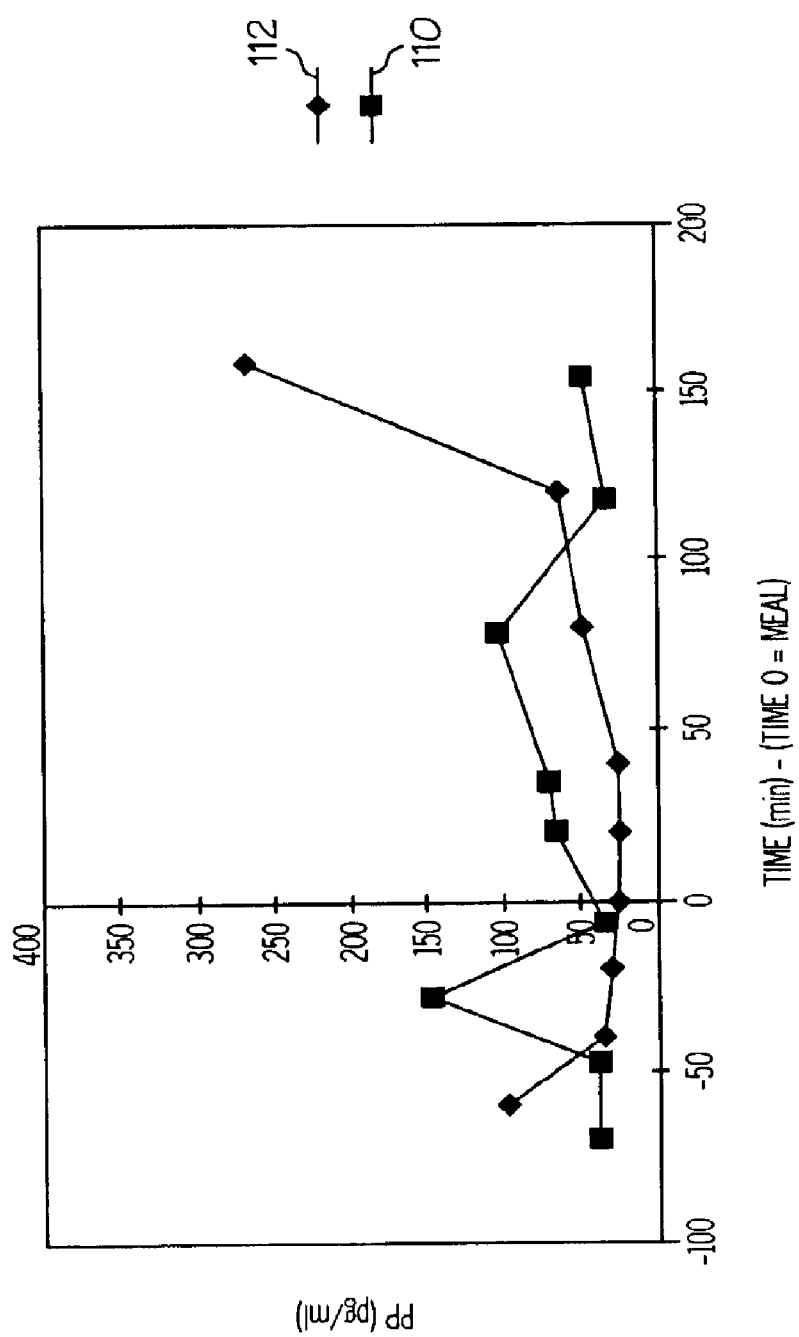

FIGS. 10a–b show graphs of a pancreatic secretion indicator, pancreatic polypeptide, before and after gastroelectric stimulation. Pancreatic polypeptide has been found to be a good indicator of the level of vagus nerve 41 stimulation on the pancreas 30, and pancreatic 30 polypeptide is an endocrine hormone and can be assessed by blood sampling but other indicators such as elastase can be used. Typically pancreatic 30 polypeptide oscillates at baseline level, increases by 4–5 fold after a meal and then returns to baseline level about 3–4 hours after the meal. Each person tested was fitted with a gastroelectric stimulator 46 selectively applying a pancreatic secretion increase signal 94 to electrodes 50 placed on the patient's stomach 26. The pancreatic 30 increase signal 94 had the following parameters: frequency 14.0 Hz, amplitude 5.0 mA, pulse width 330 $\mu$Sec, and cycled "on" for 0.1 seconds and "off" for 5.0 seconds. The test consisted of drawing a blood sample before a meal and after a meal. In the first test sequence 110, the patient's gastroelectric stimulator 46 was turned "off". In the second test sequence 112, the patient's gastroelectric Stimulator 46 was turned "on". Both natural stimulation and gastroelectric stimulation began at t=0 and continued throughout the test sequence.

FIG. 10a data was assembled with a sample of five patients 20. FIG. 10a shows that increase signal stimulation 94 did not effect baseline pancreatic 30 polypeptide, but significantly effected pancreatic 30 polypeptide after a meal. The difference in pancreatic 30 polypeptide with the gastroelectric stimulator 46 turned "off" in the first sequence 110 and turned "on" in the second sequence 112 became insignificant about three hours after the meal. Healthy persons would have a pancreatic 30 polypeptide excursion similar to that shown in the first sequence 110 graph with the gastroelectric stimulator 46 turned "off".

FIG. 10b data was assembled from testing done on a single patent 20 with a vagotomy tested in the manner described under FIGS. 10a–b. It is believed that ingestion of food causes vagus nerve 41 stimulation of the pancreas 30. A patient with a vagatomy, surgical severing of the vagus nerve 41, would not be expected to have an increase in pancreatic 30 polypeptide after ingesting food. The data in FIG. 10b is consistent with the expected results because both the first sequence 110 with gastroelectric stimulator 46 turned "off" and the second sequence 112 with the gastroelectric stimulator 46 turn "on" do not show significant pancreatic 30 stimulation. The results suggest that gastroelectric stimulation is mediated by the vagas nerve 41 because gastroelectric stimulation does not have a significant effect upon pancreatic 30 polypeptide after a meal. The high level of pancreatic 30 polypeptide about two hours after a meal with the gastroelectric stimulator 46 turned "on" cannot be explained and appears to be an error.

Although the invention has been described in detail with reference to certain preferred versions, other versions are possible. Therefore the spirit and scope of the appended claims should not be limited to the description of the preferred versions described in this disclosure.

What is claimed is:

1. A method for treating pancreatic exocrine conditions in a patient, comprising:

applying at least two electrodes to a digestive system of the patient that are coupled by at least one lead to a neurostimulator; and stimulating the digestive system with a stimulation signal generated by the neurostimulator and conveyed through the lead to the electrodes contacting the digestive system;

wherein the digestive system stimulation is transmitted to a pancreas of the patient, and wherein pancreatic exocrine secretion is influenced by the digestive system stimulation.

2. The method for treating pancreatic exocrine conditions as in claim 1, further comprising measuring a patient condition and controlling the stimulation signal in response to the measured patient condition.

3. The method of treating pancreatic exocrine conditions as in claim 2 wherein measuring the patient condition is accomplished with a sensor electrically connected to a neurostimulator.

4. The method of treating pancreatic exocrine conditions as in claim 3 wherein measuring the patient condition is accomplished by a person.

5. A method according to claim 1 wherein the electrodes contact a stomach.

6. A method according to claim 1 wherein the electrodes contact an intestine.

* * * * *